(12) United States Patent
Kim et al.

(10) Patent No.: US 12,152,650 B2
(45) Date of Patent: Nov. 26, 2024

(54) MEDICAL APPARATUS AND METHOD FOR OPERATING MEDICAL APPARATUS

(71) Applicant: SAMSUNG MEDISON CO., LTD., Gangwon-do (KR)

(72) Inventors: Namyun Kim, Seongnam-si (KR);
Simgwan Jeong, Seongnam-si (KR);
Wanki Kim, Seongnam-si (KR);
Kyeonggu Woo, Seongnam-si (KR);
Jinwoo Cha, Seongnam-si (KR);
Wonchul Choi, Seongnam-si (KR)

(73) Assignee: SAMSUNG MEDISON CO., LTD., Gangwon-Do (KR)

(*) Notice: Subject to any disclaimer, the term of this patent is extended or adjusted under 35 U.S.C. 154(b) by 227 days.

(21) Appl. No.: 17/762,562

(22) PCT Filed: Oct. 6, 2020

(86) PCT No.: PCT/KR2020/013566
§ 371 (c)(1),
(2) Date: Mar. 22, 2022

(87) PCT Pub. No.: WO2021/071198
PCT Pub. Date: Apr. 15, 2021

(65) Prior Publication Data
US 2022/0333666 A1   Oct. 20, 2022

(30) Foreign Application Priority Data

Oct. 10, 2019 (KR) .................. 10-2019-0125542
Mar. 24, 2020 (KR) .................. 10-2020-0035810

(51) Int. Cl.
*F16F 15/00*   (2006.01)
*F16F 15/03*   (2006.01)
*H05K 5/00*   (2006.01)
*H05K 5/02*   (2006.01)

(52) U.S. Cl.
CPC ............ *F16F 15/03* (2013.01); *F16F 15/002* (2013.01); *H05K 5/0018* (2022.08);
(Continued)

(58) Field of Classification Search
CPC combination set(s) only.
See application file for complete search history.

(56) References Cited

U.S. PATENT DOCUMENTS

2015/0138713 A1* 5/2015 Onda .................. G06F 1/1679
                                                                361/679.27
2019/0073077 A1   3/2019 Kim et al.
(Continued)

FOREIGN PATENT DOCUMENTS

GB       2527091 A      12/2015
JP    2001-223886 A      8/2001
(Continued)

OTHER PUBLICATIONS

Extended European Search Report issued in corresponding European Application No. 20873861.7 dated Sep. 25, 2023.
(Continued)

*Primary Examiner* — Yuzhen Shen
(74) *Attorney, Agent, or Firm* — Morgan, Lewis & Bockius LLP (57) ABSTRACT

A medical apparatus according to an example includes: a main body including an inputter configured to receive a user command; a display device positioned to be rotatable on one axis with respect to the main body, and extending along one plane; a locking device limiting a rotation of the display device with respect to the main body when pressure being smaller than first pressure is applied to the display device along a direction that is perpendicular to one surface of the display device; and an attenuator attenuating a vibration of the display device with respect to the main body when
(Continued)

pressure being smaller than the first pressure is applied to the display device along the direction that is perpendicular to the one surface of the display device.

13 Claims, 11 Drawing Sheets

(52) U.S. Cl.
CPC ........ *H05K 5/0221* (2013.01); *F16F 2222/06* (2013.01); *F16F 2228/066* (2013.01); *F16F 2230/0041* (2013.01); *F16F 2230/08* (2013.01); *F16F 2230/18* (2013.01); *H05K 5/0226* (2013.01)

(56) References Cited

U.S. PATENT DOCUMENTS

2019/0191578 A1* 6/2019 Määttä .................. H01F 7/0205
2020/0019217 A1* 1/2020 Larsen .................. G06F 1/1679
2020/0315398 A1* 10/2020 Yang .................... A47J 27/004

FOREIGN PATENT DOCUMENTS

| KR | 20-0395533 Y1 | 9/2005 |
| KR | 10-0951585 B1 | 3/2010 |
| KR | 10-2012-0041607 A | 5/2012 |
| KR | 10-2018-0078967 A | 7/2018 |
| KR | 10-2019-0027553 A | 3/2019 |

OTHER PUBLICATIONS

Supplemental European Search Report issued in corresponding European Application No. 20873861.7 dated Oct. 12, 2023.
International Search Report dated Jan. 12, 2021 issued in International Patent Application No. PCT/KR2020/013566 (with English translation).
Korean Office Action dated Aug. 20, 2024 issued in Korean Patent Application No. 10-2020-0035810 (with English translation).

* cited by examiner

MEDICAL APPARATUS AND METHOD FOR OPERATING MEDICAL APPARATUS

CROSS-REFERENCE OF RELATED APPLICATIONS

This application is the U.S. National Phase under 35 U.S.C. § 371 of International Patent Application No. PCT/KR2020/013566, filed on Oct. 6, 2020, which in turn claims the benefit of Korean Application Nos. 10-2019-0125542, filed on Oct. 10, 2019 and 10-2020-0035810, filed on Mar. 24, 2020, the entire disclosures of which applications are incorporated by reference herein.

TECHNICAL FIELD

The present disclosure relates to a medical apparatus and a method for operating the medical apparatus.

BACKGROUND ART

As medical apparatuses for obtaining medical images about bodies, an ultrasonic apparatus, a magnetic resonance imaging (MRI) apparatus, a computed tomography (CT) apparatus, an x-ray apparatus, etc. are widely used. Due to reasons, such as the resolution of images, the sizes of apparatuses, etc., these apparatuses may photograph body parts or the entire bodies. Also, these apparatuses may photograph the entire body at a time, or photograph body parts by several times and then synthesize the photographed images to obtain a synthesized image about the entire body.

A medical apparatus for obtaining medical images about bodies includes a display for displaying photographed images for users, for example, doctors. The display is connected to a main body including a control panel for enabling users to input commands, a controller, etc.

Lately, touch screen type displays to enable users to input commands directly through the displays are used. When pressure is applied to a display rotatably connected to a main body, the display may vibrate. When the display vibrates, a user's view may sense wobble of the display, which deteriorates user convenience.

DISCLOSURE

Technical Problem

The present disclosure is directed to providing a medical apparatus including a display device capable of preventing vibrations that are generated by pressure applied from outside.

The present disclosure is directed to providing a method for operating a medical apparatus capable of sensing a magnitude of pressure applied from outside and minimizing (minimizing up to a small vibration level that a user cannot recognize) a vibration of a display device, the vibration generated by the pressure applied from the outside according to the magnitude of the applied pressure.

Technical Solution

A medical apparatus according to an example includes: a main body including an inputter configured to receive a user command; a display device positioned to be rotatable on one axis with respect to the main body, and extending along one plane; a locking device limiting a rotation of the display device with respect to the main body when pressure being smaller than first pressure is applied to the display device along a direction that is perpendicular to one surface of the display device; and an attenuator attenuating a vibration of the display device with respect to the main body when pressure being smaller than the first pressure is applied to the display device along the direction that is perpendicular to the one surface of the display device.

The medical apparatus may further include a sensor configured to sense pressure applied to the display device along the direction that is perpendicular to the one surface of the display device.

The medical apparatus may further include a controller configured to control operations of the attenuator and the locking device according to a magnitude of the pressure sensed by the sensor.

A plurality of attenuators may be provided, and the plurality of attenuators may be spaced from each other with a preset distance from the locking device.

The attenuator may include a first attenuator and a second attenuator, and the first attenuator and the second attenuator may be spaced from each other on an upper area of the display device.

The attenuator may include a third attenuator and a fourth attenuator, and the third attenuator and the fourth attenuator may be spaced from each other on a lower area of the display device.

The attenuator may further include: a first attenuating member positioned on the display device; and a second attenuating member positioned on the main body, and attached/detached to/from the first attenuating member.

The first attenuating member may be attached to the second attenuating member by a magnetic force.

Any one of the first attenuating member and the second attenuating member may include a permanent magnet, and the remaining one of the first attenuating member and the second attenuating member may include a magnetic material.

Any one of the first attenuating member and the second attenuating member may include a permanent magnet.

The medical apparatus may further include: a first current supplier supplying current to the permanent magnet; and a first switch turning on/off a connection between the first current supplier and the permanent magnet according to a magnitude of pressure applied to the display device.

The locking device may further include: a first locking member positioned on the display device; and a second locking member positioned on the main body, and attached/detached to/from the first locking member.

When pressure being smaller than the first pressure is applied to the display device, the first locking member may be attached to the second locking member and a rotation of the display device with respect to the main body is limited, and, when pressure being greater than or equal to the first pressure is applied to the display device, the first locking member may be separated from the second locking member and the display device may rotate with respect to the main body.

The first locking member may be attached to the second locking member by a magnetic force.

Any one of the first locking member and the second locking member may include a permanent magnet, and the remaining one of the first locking member and the second locking member may include a magnetic material.

Any one of the first locking member and the second locking member may include a permanent magnet.

The medical apparatus may further include: a second current supplier supplying current to the permanent magnet;

and a second switch turning on/off a connection between the second current supplier and the permanent magnet according to a magnitude of pressure applied to the display device.

A method for operating a medical apparatus including a main body and a display device hinge-coupled with the main body, according to an example, includes: sensing pressure applied to the display device; setting, when the pressure applied to the display device is sensed to be smaller than first pressure, a mode of the display device to a use state in which the display device is fixed with respect to the main body; and attenuating, when the mode of the display device is set to the use state, a vibration of the display device with respect to the main body.

The attenuating of the vibration of the display device may include attaching a first attenuating member positioned on the display device to a second attenuating member positioned on the main body.

The first attenuating member may be attached to the second attenuating member by a magnetic force.

Advantageous Effects

A medical apparatus according to an example may suppress vibrations (wobble, noise, etc.) that may be generated in a display device by pressure applied from outside, thereby improving the quality of the apparatus.

A medical apparatus according to an example may suppress or minimize vibrations to a level which a user cannot recognize, thereby reducing the fatigue in use.

A medical apparatus according to an example may sense a magnitude of pressure applied from outside, and minimize vibrations of a display device, which are generated by the pressure applied from the outside, according to the magnitude of the pressure applied from the outside.

DESCRIPTION OF DRAWINGS

The embodiments of the disclosure may be easily understood by combining the following detailed description with the accompanying drawings, and reference numerals mean structural elements.

MODES OF THE INVENTION

The present specification will describe the principles of embodiments of the disclosure and disclose the embodiments to clarify the scope of rights of the claims of the disclosure and for those skilled in the technical art to which the embodiments of the disclosure belong to embody the embodiments of the disclosure. The disclosed embodiments may be implemented in various forms.

Throughout this specification, like reference numerals will refer to like components. The present specification does not describe all elements of the embodiments, and descriptions about content being general in the technical art to which the embodiments of the disclosure belong or overlapping content between the embodiments will be omitted. As used herein, the terms "part" or "portion" may be implemented as software or hardware, and according to embodiments, a plurality of "parts" or "portions" may be implemented as a single unit or element, or a single "part" or "portion" may include a plurality of units or elements. Hereinafter, the embodiments of the disclosure and an operation principle of the embodiments will be described with reference to the accompanying drawings.

Figure 1:
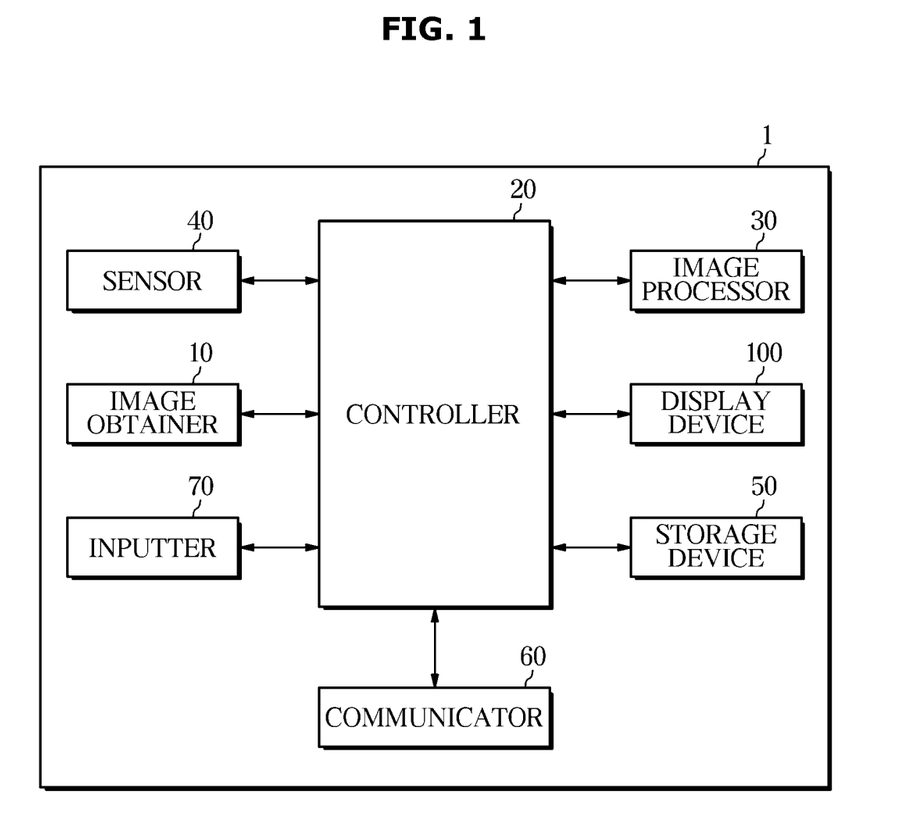
FIG. 1 is a block diagram showing a configuration of a medical apparatus according to an embodiment.
Figure 2:
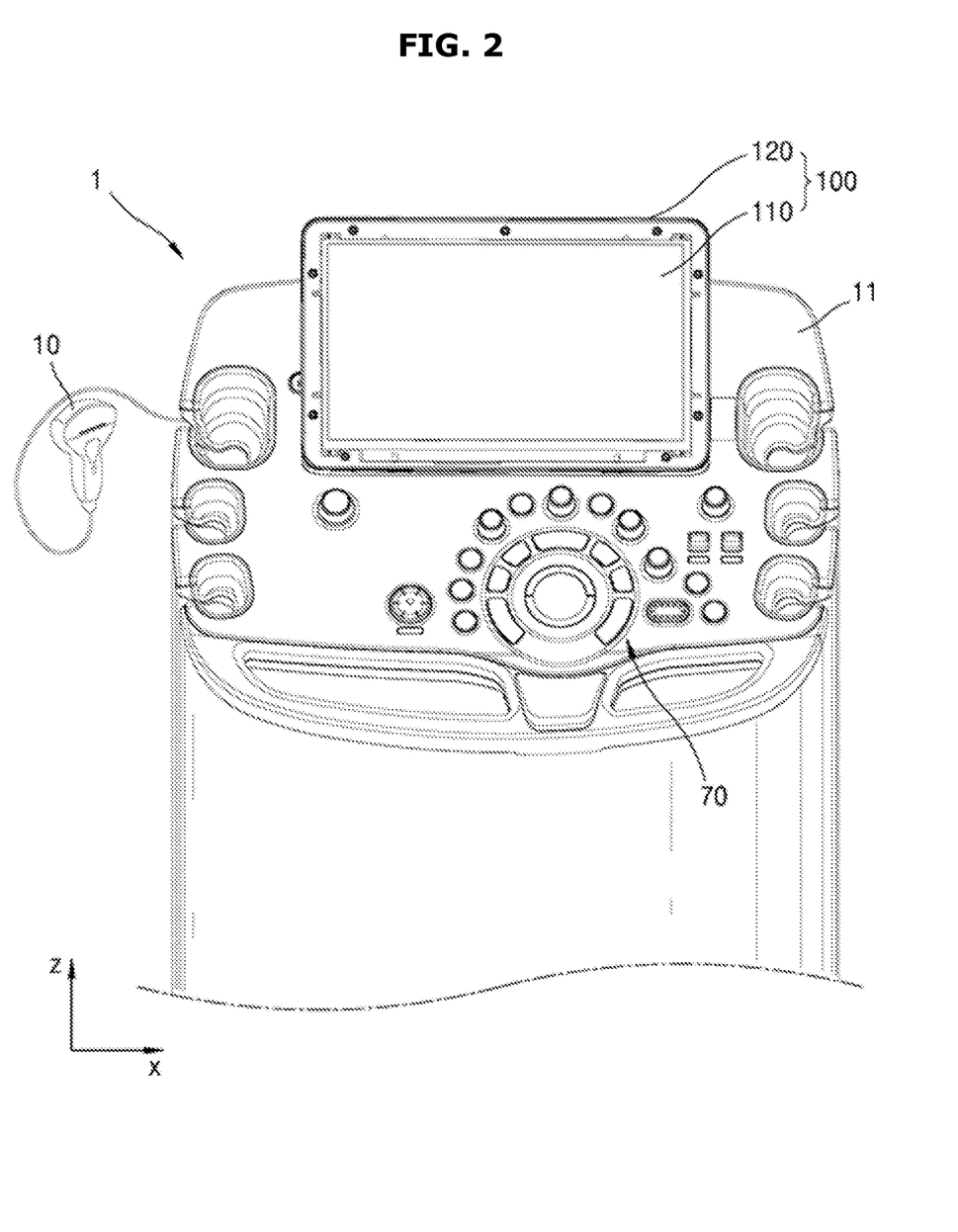
FIG. 2 is a perspective view of a medical apparatus according to an embodiment.

FIG. 1 is a block diagram showing a configuration of a medical apparatus according to an embodiment. FIG. 2 is a perspective view of a medical apparatus according to an embodiment.

Referring to FIGS. 1 and 2, a medical apparatus 1 according to an embodiment may include an image obtainer 10, a controller 20, an image processor 30, a sensor 40, a storage device 50, a communicator 60, an inputter 70, and a display device 100. In this case, for example, the medical apparatus 1 may include a main body 11 for accommodating the controller 20, the image processor 30, the sensor 40, the storage device 50, the communicator 60, and the inputter 70.

The image obtainer 10 may be an image obtaining apparatus for obtaining medical images about a subject. For example, the image obtainer 10 may include an ultrasonic apparatus, a magnetic resonance imaging (MRI) apparatus, a computed tomography (CT) apparatus, and an x-ray apparatus, although not limited thereto. For example, the image obtainer 10 may be integrated into the medical apparatus 1, or implemented as a separation type connected to the medical apparatus 1 in a wired or wireless manner. Also, the medical apparatus 1 may include a single or plurality of image obtainers 10 according to an implementation type.

The controller 20 may control overall operations of the medical apparatus 1 and signal flow between internal components of the medical apparatus 1. The controller 20 according to an example may include a memory storing programs or data for performing functions of the medical apparatus 1, and a processor for processing the programs or data. Also, the controller 20 may control operations of an attenuator 400 and a locking device 300 according to a magnitude of pressure sensed by the sensor 40 which will be described below.

The image processor 30 may generate an image by using image data generated by the image obtainer 10.

Figure 6A:
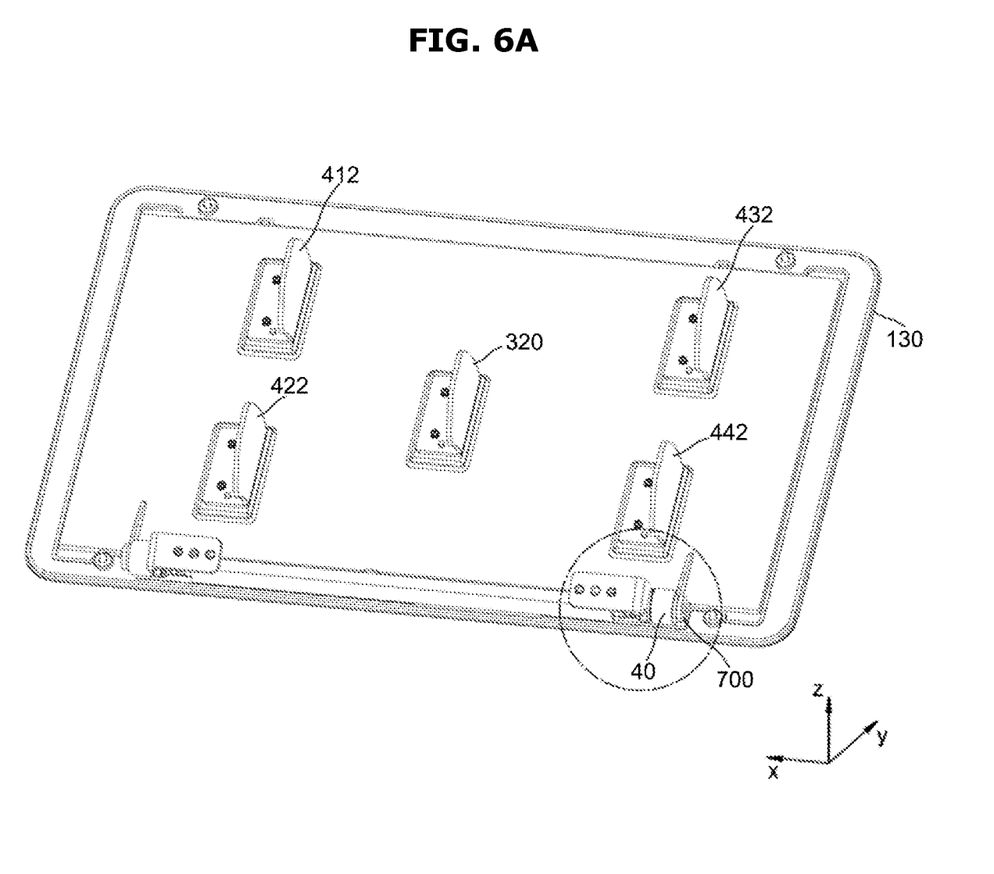
FIG. 6A is a bottom perspective view of a display device according to an embodiment.
Figure 6B:
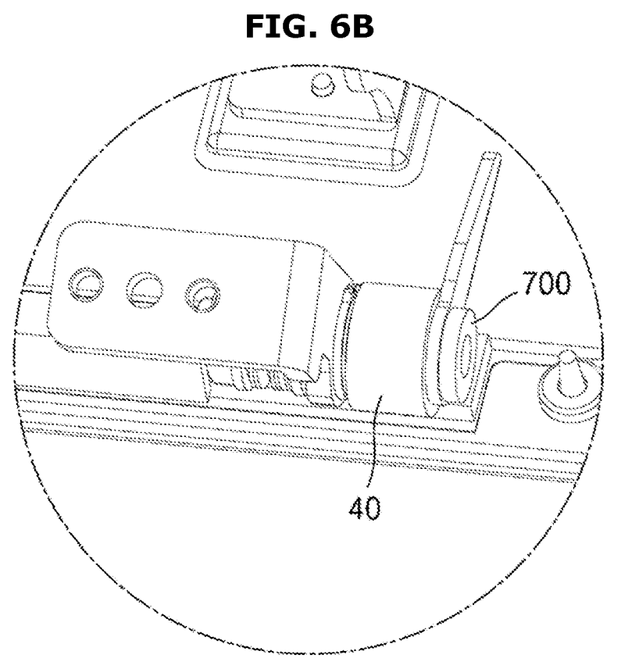
FIG. 6B is a perspective view of a hinge according to an embodiment.

The sensor 40 may be a sensor for sensing external pressure applied to the display device 100. For example, the sensor 40 may sense pressure perpendicularly applied to a surface of a display 110 provided in the display device 100. For example, a user may apply pressure for rotating the display device 100 with respect to the main body 11. At this time, pressure may be applied to the display device 100 in the same direction as that of preset first pressure $F_1$. The sensor 40 may sense a magnitude of the pressure having the same direction as that of the first pressure $F_1$ (see FIG. 3) and applied to the display device 100. The sensor 40 according to an example may be positioned in a hinge 700, as shown in FIG. 6B, to sense pressure applied to the display device 100. However, a location of the sensor 40 according to the disclosure is not limited to the hinge 70, and the sensor 40 according to an example may be positioned at an arbitrary area of the display device 100 where a user applies pressure to the display device 100. For example, a touch sensor positioned inside the display 110 of the display device 100 may be used as the sensor 40 according to an embodiment for sensing pressure.

The storage device 50 may store various data or programs for driving and controlling the medical apparatus 1 and the first pressure $F_1$ which is a reference pressure value for rotating the display device 100.

The medical apparatus 1 according to an example may include the communicator 60, and may be connected to an external device (for example, a server or a portable device (a smart phone, a tablet PC, a wearable device, etc.)) through the communicator 60.

The communicator 60 may include one or more components for enabling communications with an external device, and for example, the communicator 60 may include at least one of a short range communication module, a wired communication module, and a wireless communication module.

The communicator 60 may receive a control signal and data from an external device, transfer the received control signal to the controller 20, and enable the controller 20 to control the medical apparatus 1 according to the received control signal.

The inputter 70 may receive a user input for controlling the medical apparatus 1. For example, the user input may include an input of operating a button, a key pad, a mouse, a track ball, a jog switch, a knop, etc., an input of touching a touch pad or a touch screen, a voice input, a motion input, a biometric information input (for example, iris recognition, fingerprint recognition, etc.), etc., although not limited thereto.

The display device 100 may display information that is processed by the medical apparatus 1. For example, the display device 100 may display an image generated by the image processor 30, or a graphic user interface (GUI) for requesting a user's input.

For example, the display device 100 may include at least one of a liquid crystal display, a thin film transistor-liquid crystal display, an organic light-emitting diode, a flexible display, a three-dimensional (3D) display, and an electrophoretic display.

The display device 100 may include the display 110 for displaying medical images and a user interface, and a housing 120 forming an outer appearance of the display device 100. The display 110 may be positioned on a front side of the display device 100. The display device 100 according to an example may be tilted at a preset angle with respect to the main body 11. The medical apparatus 1 according to an example may further include a connecting portion 90 (see FIG. 3) connecting the display device 100 to the main body 11. Hereinafter, a connection structure for connecting the display device 100 to the main body 11 by using the connecting portion 90, a structure in which the display device 100 is tilted or vibrates with respect to the main body 11 according to a magnitude of pressure applied from outside, and a structure for minimizing such tilting or vibrations will be described.

Figure 3:
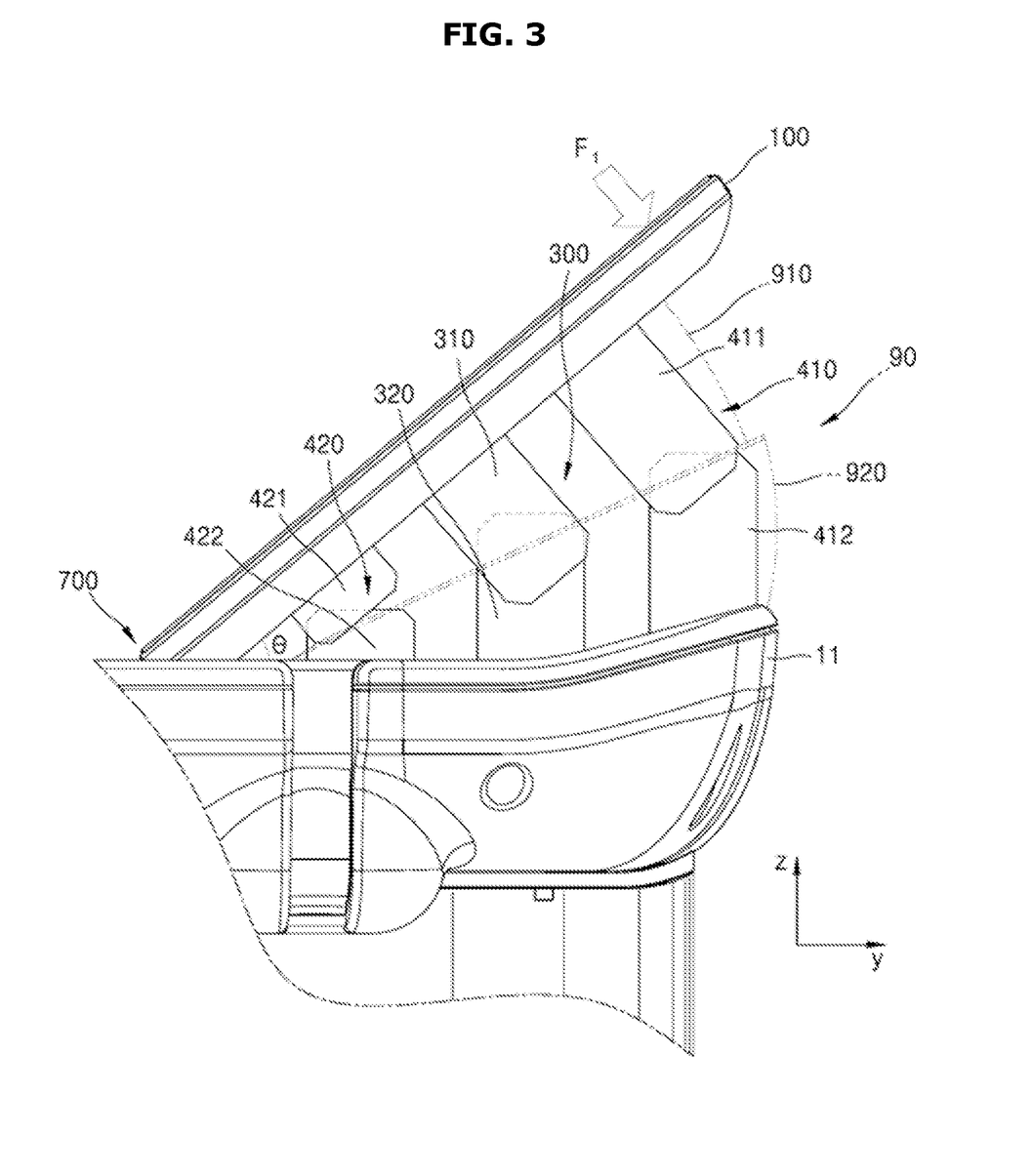
FIG. 3 is a side view of a medical apparatus according to an embodiment.
Figure 4:
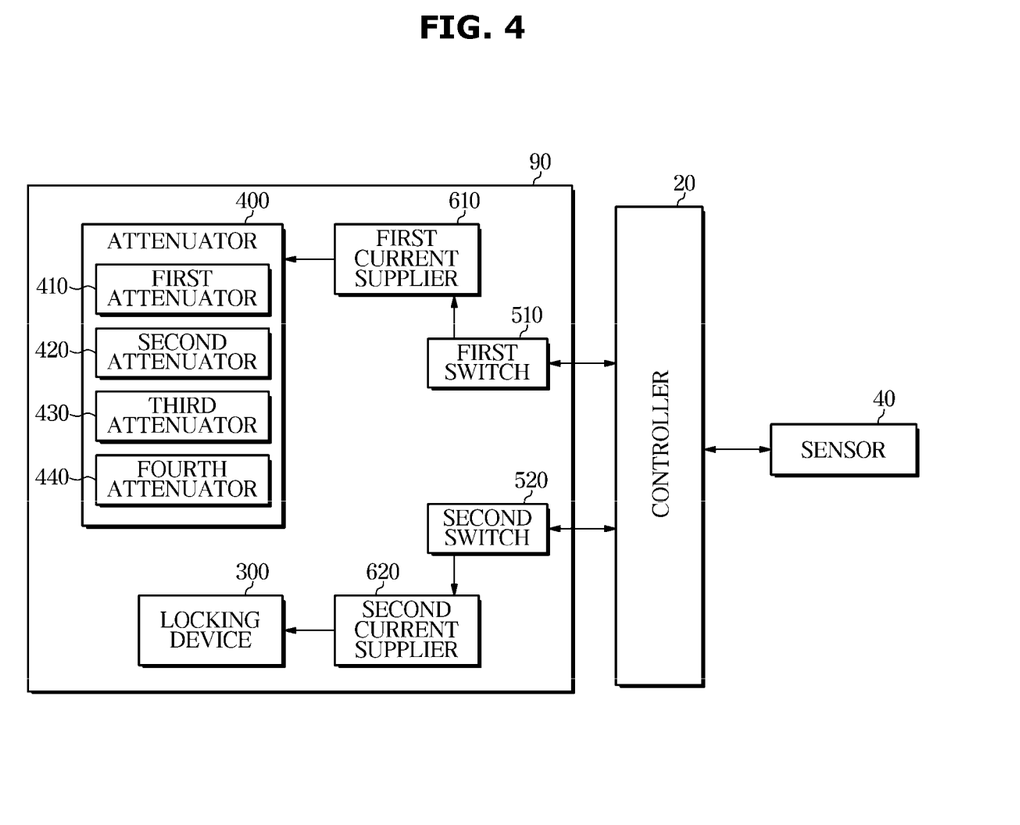
FIG. 4 is a block diagram of a connecting portion according to an embodiment.
Figure 5:
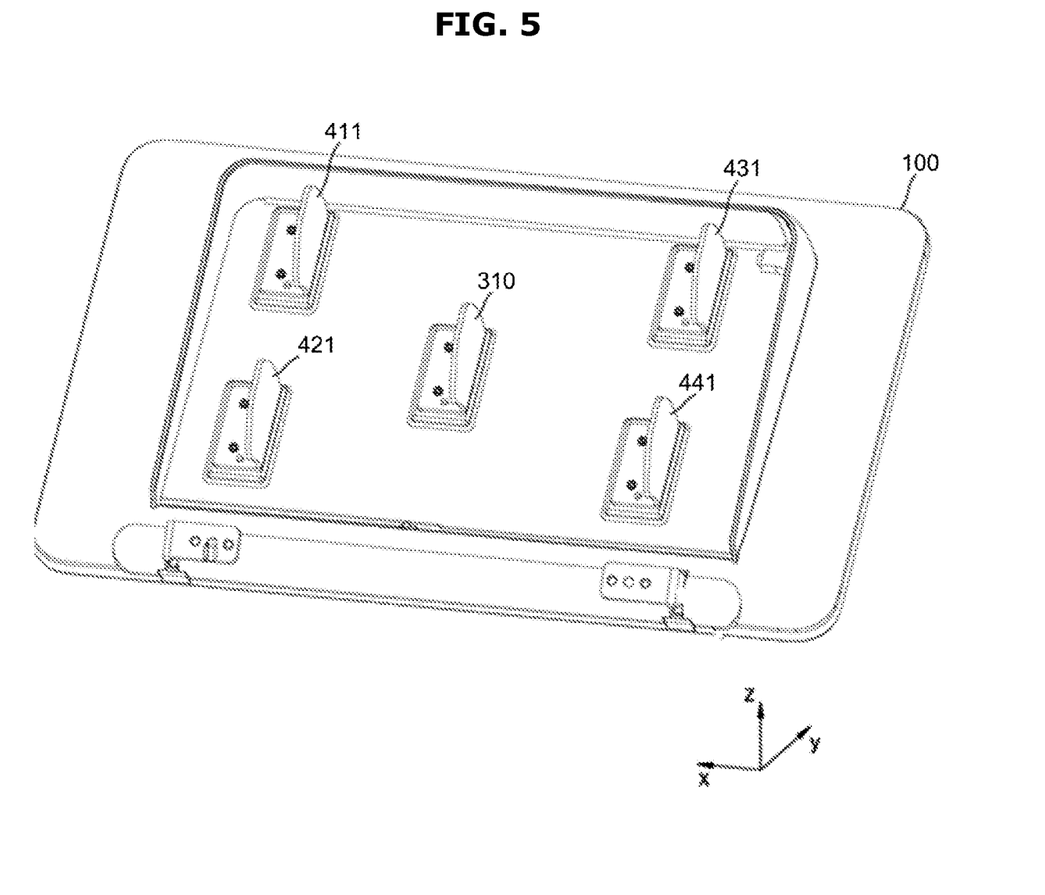
FIG. 5 is a perspective view of a bracket according to an embodiment.

FIG. 3 is a side view of a medical apparatus according to an embodiment. FIG. 4 is a block diagram of a connecting portion according to an embodiment. FIG. 5 is a perspective view of a bracket according to an embodiment. FIG. 6A is a bottom perspective view of a display device according to an embodiment. FIG. 6B is a perspective view of a hinge according to an embodiment.

Referring to FIGS. 3 and 4, the connecting portion 90 according to an example may be a connecting member positioned between the display device 100 and the main body 11 and connecting the display device 100 to the main body 11 such that the display device 100 is rotatable on one axis (X-axis) with respect to the main body 11.

For example, the display device 100 may be positioned in a first state (hereinafter, referred to as a 'rotation state') in which the display device 100 rotates on one axis (X-axis) with respect to the main body 11 by external pressure, for example, pressure applied by a user. Also, the display device 100 may be positioned in a second state (hereinafter, referred to as a 'use state') in which a location of the display device 100 is fixed with respect to the main body 11.

To implement the rotation state and the use state as described above, the connecting portion 90 according to an example may include the locking device 300, the attenuator 400, a first switch 510, a second switch 520, a first current supplier 610, a second current supplier 610, the hinge 700 (see FIG. 6A), a first case 910, and a second case 920.

The locking device 300 may be a rotation limiter for fixing a relative location of the display device 100 with respect to the main body 11. The locking device 300 according to an example may include a first locking member 310 positioned on a rear surface of the display device 100 and a second locking member 320 positioned on the main body 11. For example, the first locking member 310 may be fixed at a center portion of the display device 100. The second locking member 320 may be fixed at a center portion of a bracket 130 provided in the main body 11.

Also, for example, the first locking member 310 and the second locking member 320 may be provided in a shape of a flat plate with a preset area. Also, one or both of the first locking member 310 and the second locking member 320 may include a material with a magnetic force. For example, any one of the first locking member 310 and the second locking member 320 may include a permanent magnet, and the remaining one may include a magnet or a magnetic material capable of generating an attraction force with the permanent magnet, although not limited thereto. However, both the first locking member 310 and the second locking member 320 may include a permanent magnet, or any one of the first locking member 310 and the second locking member 320 may include a magnet while the remaining one may include a magnetic material.

According to an example, the first pressure $F_1$ applied to the display device 100 may be set, for example, in a range of 1.2 kgf to 1.8 kgf. In this case, the preset first pressure $F_1$ may be stored in the storage device 50. For example, when pressure being greater than/equal to the first pressure $F_1$ is applied to the display device 100 and the display device 100 rotates on one axis (X-axis) with respect to the main body 11, that is, in a rotation state, the first locking member 310 may be separated from the second locking member 320. Meanwhile, when pressure being smaller than the first pressure $F_1$ is applied to the display device 100 and the display device 100 is fixed with respect to the main body 11, that is, in a use state, the first locking member 310 may be attached to the second locking member 320 by a magnetic force. Accordingly, a location of the display device 100 with respect to the main body 11 may be fixed.

The attenuator 400 may be an attenuating member for attenuating vibrations of the display device 100 with respect to the main body 11. The attenuator 400 according to an example may prevent an area of the display device 100 from wobbling by pressure applied from the outside, for example, pressure that may be generated by a user's touch input.

For example, when the display device 100 shown in FIG. 3 is simplified in a shape of a cantilever, the display device 100 may be a cantilever having mass m. In this case, when a unique modulus of elasticity of the display device 100 is set to E (Young's Modulus), a secondary moment of inertia for the shape of the display device 100 is set to I (Moment of inertia), a force caused by a user's touch input is set to f, a linear distance from the hinge 700 according to the user's touch input is set to L, and an attenuation coefficient of the attenuator 400 suppressing vibrations is set to c, a vibration motion equation of the display device 100 may be Equation 1 below.

$$f = m\ddot{X}(t) + c\dot{X}(t) + k_{beam}X(t) \text{ when, } k_{beam} = \frac{3EI}{L^3}. \quad \text{[Equation 1]}$$

Herein, X(t) may be a scale representing displacement of the display device 100 over time and called the term 'amplitude' in vibeology. A magnitude of vibration felt by a user may be in proportion to the amplitude. The motion equation is expressed with respect to the amplitude to obtain Equation 2.

$$X(t) = \frac{1}{k_{beam}}(f - m\ddot{X}(t) - c\dot{X}(t)). \quad \text{[Equation 2]}$$

The medical apparatus 1 according to an example may include a vibration suppressing device for reducing the above-described amplitude, in other words, the attenuator 400 which is a structure for increasing an attenuation coefficient c.

The attenuator 400 according to an example may be provided as a plurality of pieces that are spaced from each other throughout an entire rear surface of the display device 100. For example, the attenuator 400 may include first to fourth attenuators 410 to 440, wherein a first attenuator 410 and a second attenuator 420 may be spaced from each other on an upper area of the display device 100 and a third attenuator 30 and a fourth attenuator 440 may be spaced from each other on a lower area of the display device 100.

Also, the first to fourth attenuators 410 to 440 according to an example may be positioned above or below the locking device 300. For example, when the locking device 300 is positioned at the center portion of the display device 100, the first attenuator 410 and the third attenuator 430 may be positioned above the locking device 300, and the second attenuator 420 and the fourth attenuator 440 may be positioned below the locking device 300. Accordingly, even when a user's touch input is applied to an upper corner or a lower corner of the display 110 provided in the display device 100, as well as when a user's touch input is applied to the center portion of the display 110, vibrations of the display device 100 with respect to the main body 11 may be prevented, although not limited thereto.

However, four or more attenuators 400 may be provided to be spaced from each other throughout the entire area of the display device 100, such as a right surface, a left surface, an upper corner, or a lower corner of the display device 100. Accordingly, even when a user's touch input is applied to the entire area of the display 110 provided in the display device 100, for example, the right or left surface of the display 110, vibrations of the display device 100 with respect to the main body 11 may be prevented.

The first to fourth attenuators 410 to 440 according to an example may include, as shown in FIGS. 5 and 6A, first attenuating members 411, 421, 431, and 441 positioned on the rear surface of the display device 100, and second attenuating members 412, 422, 432, and 442 positioned on the main body 11. For example, the second attenuating members 412, 422, 432 and 442 may be fixed on the bracket 130 provided in the main body 11. The first attenuating members 411, 421, 431, and 441 and the second attenuating members 412, 422, 432, and 442 included in the first to fourth attenuators 410 to 440 may have the substantially same configuration, and therefore, the following description will be given based on the first attenuating member 411 and the second attenuating member 412 included in the first attenuator 410.

The first attenuating member 411 and the second attenuating member 412 according to an example may be provided in a shape of a flat plate having a preset area. Also, one or both of the first attenuating member 411 and the second attenuating member 412 may include a material with a magnetic force. For example, any one of the first attenuating member 411 and the second attenuating member 412 may include a permanent magnet, and the remaining one may include a magnet or a magnetic material capable of generating an attraction force with the permanent magnet, although not limited thereto. However, both the first attenuating member 411 and the second attenuating member 412 may include a permanent magnet, or any one of the first attenuating member 411 and the second attenuating member 412 may include a magnet while the remaining one may include a magnetic material.

In the above-described embodiment, the attenuator 400 may include a magnet or a magnetic material, although not limited thereto. According to an example, the attenuator 400 may locate a buffer member between the first attenuating member 411 and the second attenuating member 412 to attenuate vibrations of the display device 100 with respect to the main body 11. Also, according to an example, the attenuator 400 may include a pneumatic cylinder and a ball plunger positioned between the main body 11 and the display device 100 to attenuate vibrations of the display device 100 with respect to the main body 11.

The hinge 700 may be a connecting member including a rotating shaft on which the display device 100 is rotatable with respect to the main body 11. For example, the hinge 700 may be positioned in the main body 11, more specifically, at a lower end of the bracket 130. In this case, the sensor 40 may be attached to the hinge 70 to sense rotation pressure applied to the display device 100 from the outside.

The first case 910 and the second case 920 may be accommodating members capable of accommodating the locking device 300 and the attenuator 400. For example, the first case 910 and the second case 920 may be fixed to the display device 100 and the main body 11, respectively. Also, the first case 910 and the second case 920 may overlap with each other when the display device 100 rotates with respect to the main body 11. Accordingly, the first case 910 and the second case 920 may not interfere with each other even when the display device 100 rotates with respect to the main body 11, and accordingly, the display device 100 may be positioned adjacent to the main body 11.

As described above, the display device 100 may be positioned in the rotation state in which the display device 100 rotates on one axis (X-axis) with respect to the main body 11, and in the use state in which a location of the display device 100 is fixed with respect to the main body 11. The rotation state and the use state may be determined according to a magnitude of pressure applied to the display device 100 from the outside.

For example, the rotation state in which the display device 100 rotates on one axis (X-axis) with respect to the main body 11 may be a state in which the display device 100 needs to be tilted with respect to the main body 11, and, in the rotation state, a relatively great force, for example, pressure being greater than/equal to the first pressure $F_1$ may be applied to rotate the display device 100. Meanwhile, in the use state in which the location of the display device 100 needs to be fixed with respect to the main body 11, a touch input (for example, pressure being smaller than the first pressure $F_1$) for operating the display device 100 may be applied.

Hereinafter, an embodiment for controlling operations of the locking device 300 and the attenuator 400 by using the first switch 510, the second switch 520, the first current supplier 610, and the second current supplier 620 according to a magnitude of pressure applied to the display device 100, and implementing the rotation state and the use state for the display device 100 accordingly will be described in more detail.

Figure 7A:
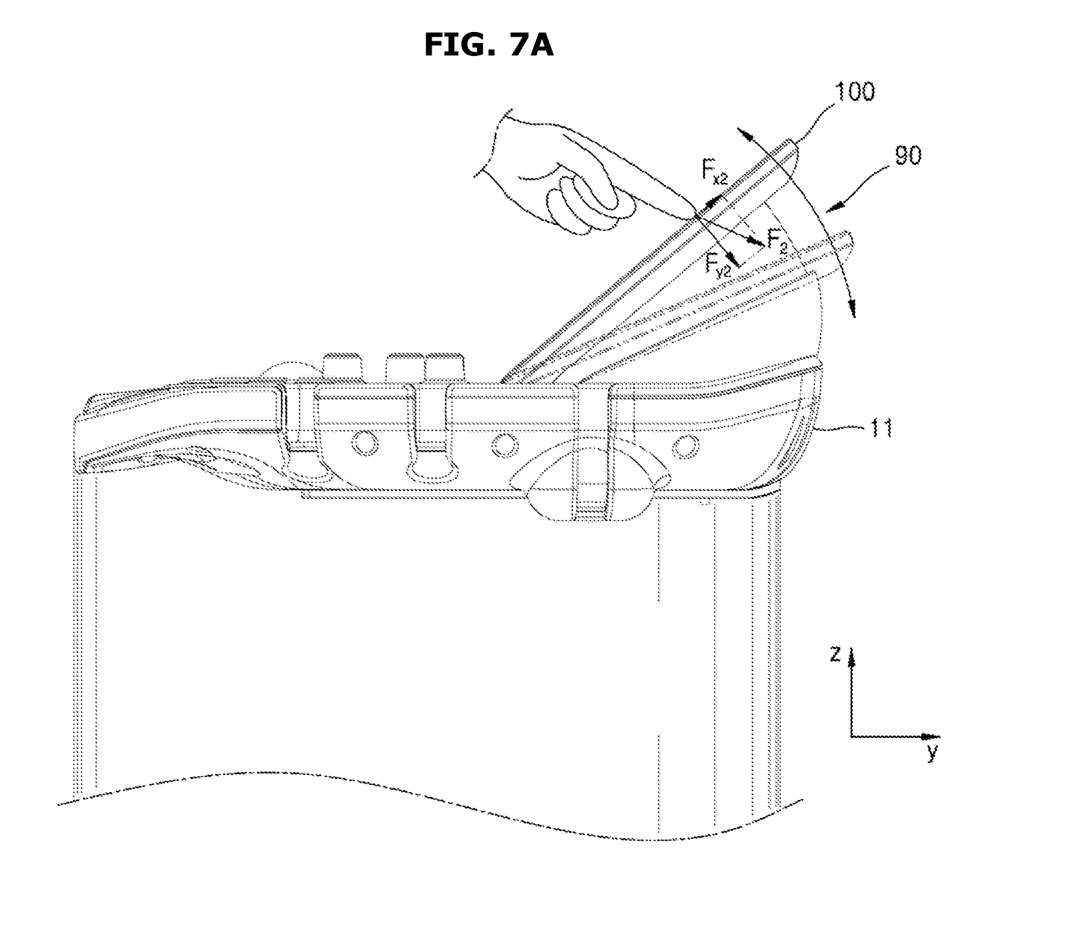
FIG. 7A is a side view of a medical apparatus showing a rotation state according to an embodiment.
Figure 7B:
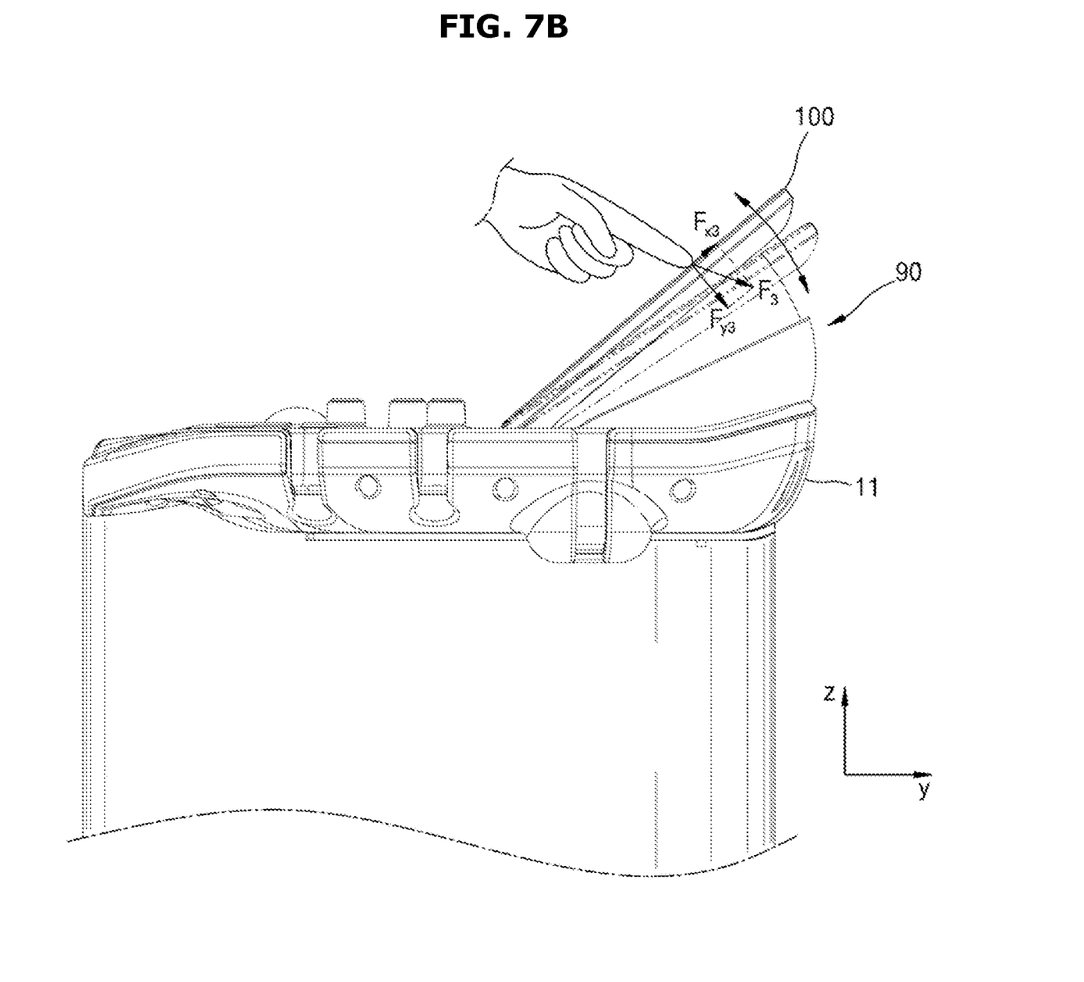
FIG. 7B is a side view of a medical apparatus showing a use state according to an embodiment.
Figure 8:
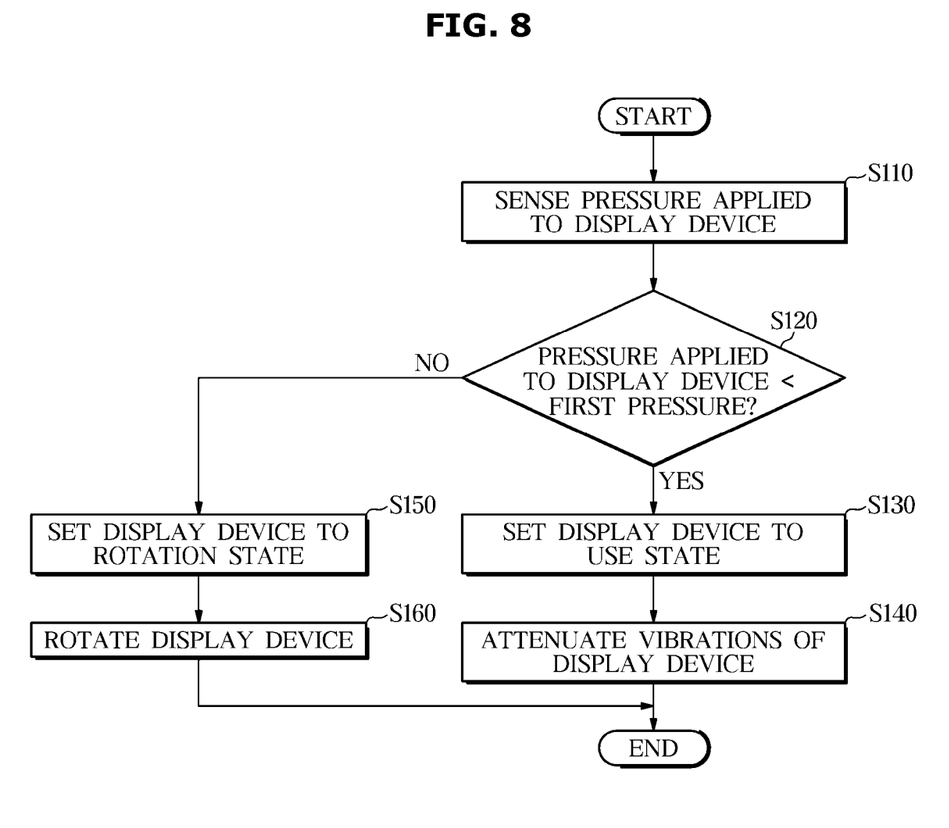
FIG. 8 is a flowchart showing an operation method of a medical apparatus according to an embodiment.

FIG. 7A is a side view of a medical apparatus showing a rotation state according to an embodiment. FIG. 7B is a side view of a medical apparatus showing a use state according to an embodiment. FIG. 8 is a flowchart showing an operation method of a medical apparatus according to an embodiment.

Referring to FIG. 7A, according to an embodiment, a user may apply pressure $F_2$ for adjusting a tiling angle of the display device 100 with respect to the main body 11. At this time, pressure applied to the display device 100 to rotate the display device 100 with respect to the main body 11 may be second pressure $F_{y2}$ that is perpendicular to one surface of the display 110 of the display device 100. In the rotation state in which the display device 100 rotates with respect to the main body 11, a magnitude of the second pressure $F_{y2}$ may be greater than/equal to the preset first pressure $F_1$. According to an example, the second pressure $F_{y2}$ applied to the display device 100 may be greater than the preset first pressure $F_1$. For example, a ratio $F_{y2}/F_1$ of the second pressure $F_{y2}$ to the first pressure $F_1$ may be greater than 1 and smaller than/equal to 4. For example, the first pressure $F_1$ may be set in a range of 1.2 kgf to 1.8 kgf and stored in the storage device 50. In this case, the second pressure $F_{y2}$ may be set in a range of 1.6 kgf to 4.8 kgf and stored in the storage device 50, although not limited thereto. However, a magnitude of the second pressure $F_{y2}$ may be set in various ranges that are greater than a magnitude of the preset first pressure $F_1$.

Meanwhile, referring to FIG. 7B, according to an embodiment, a user may apply pressure $F_3$ for inputting a touch input to the display device 100. At this time, pressure applied to the display device 100 to rotate the display device 100 with respect to the main body 11 may be third pressure $F_{y3}$ that is perpendicular to one surface of the display 110 of the display device 100. In a fixed state in which the display device 100 is fixed with respect to the main body 11, a magnitude of the third pressure $F_{y3}$ may be smaller than the preset first pressure $F_1$. According to an example, the third pressure $F_{y3}$ applied to the display device 100 may be smaller than the preset first pressure $F_1$. For example, a ratio $F_{y3}/F_1$ of the third pressure $F_{y3}$ to the first pressure $F_1$ may be greater than/equal to 0.028 and smaller than/equal to 0.75. For example, when the first pressure $F_1$ is set in a range of 1.2 kgf to 1.8 kgf and stored in the storage device 50, the third pressure $F_{y3}$ may be set in a range of 0.05 kgf to 0.9 kgf and stored in the storage device 50, although not limited thereto. However, a magnitude of the third pressure $F_{y3}$ may be set in various ranges that are smaller than the preset first pressure $F_1$.

Referring to FIGS. 4, 7A, 7B, and 8, according to an example, when pressure is applied to the display device 100 form the outside, the sensor 40 may sense the pressure applied to the display device 100 (S110). For example, the pressure sensed by the sensor 40 may be pressure $F_{y2}$ or $F_{y3}$ that is perpendicular to one surface of the display 110 of the display device 100, as shown in FIGS. 7A and 7B.

Then, the controller 20 may determine whether a magnitude of the pressure $F_{y2}$ or $F_{y3}$ sensed by the sensor 40 is greater than/equal to or smaller than the preset first pressure $F_1$ (S120). According to an example, magnitudes of the first pressure $F_1$, the second pressure $F_{y2}$, and the third pressure $F_{y3}$, based on which the use state and the rotation state of the display device 100 are determined, may have been set in advance and stored in the storage device 50. For example, the magnitude of the first pressure $F_1$ may be greater than that of a user's touch input, for example, the third pressure $F_{y3}$ and smaller than that of pressure for rotating the display device 100 by a user, for example, the second pressure $F_{y2}$. For example, a ratio $F_{y2}/F_1$ of the second pressure $F_{y2}$ to the first pressure $F_1$ may be set to be greater than 1 and smaller than/equal to 4 and stored in the storage device 50. For example, the ratio $F_{y3}/F_1$ of the third pressure $F_{y3}$ to the first pressure $F_1$ may be set to be greater than/equal to 0.028 and smaller than/equal to 0.75 and stored in the storage device 50, although not limited thereto. However, the ratio $F_{y2}/F_1$ of the second pressure $F_{y2}$ to the first pressure $F_1$ and the ratio $F_{y3}/F_1$ of the third pressure $F_{y3}$ to the first pressure $F_1$ may change according to an environment.

Then, when the magnitude of the pressure $F_{y3}$ sensed by the sensor 40 is smaller than the first pressure $F_1$, the display device 100 may set to the use state (S130). According to an example, when the third pressure $F_{y3}$ sensed by the sensor 40 is smaller than the first pressure $F_1$, for example, when the ratio $F_{y3}/F_1$ of the third pressure $F_{y3}$ to the first pressure $F_1$ is greater than/equal to 0.028 and smaller than/equal to 0.75, the controller 20 may apply a control signal for turning off the first switch 510. The first current supplier 610 may supply no current to the attenuator 400, more specifically, the first attenuating member 411 by the first switch 510 that has received an off signal from the controller 20.

Also, the controller 20 may apply a control signal for turning off the second switch 520. The second current supplier 620 may supply no current to the locking device 300, more specifically, the first locking member 310 by the second switch 520 that has received an off signal from the controller 20. When no current is supplied to the first locking member 310, the first locking member 310 may maintain magnetism, and accordingly, the first locking member 310 may be maintained in a state in which the first locking member 310 is attached to the second locking member 320. Because a state in which the first locking member 310 positioned on the display device 100 is attached to the second locking member 320 positioned on the main body 11 is maintained, the display device 100 may be maintained in the use state.

Then, vibrations of the display device 100 may be attenuated by the attenuator 400 (S140). For example, when no current is supplied to the first attenuating member 411, the first attenuating member 411 may have magnetism, and accordingly, the first attenuating member 411 may be attached to the second attenuating member 412. Because the first attenuating member 411 positioned on the display device 100 is attached to the second attenuating member 412 positioned on the main body 11, the display device 100 may be prevented from vibrating even when pressure applied from the outside, for example, a user's touch input is applied. Accordingly, as shown in FIG. 7B, even when a user's touch input is applied to the display device 100, vibrations of the display device 100 with respect to the main body 11 may be minimized.

Then, when a magnitude of the second pressure $F_{y2}$ sensed by the sensor 40 is greater than or equal to the first pressure $F_1$, for example, when a ratio $F_{y2}/F_1$ of the second pressure $F_{y2}$ to the first pressure $F_1$ is greater than 1 and smaller than/equal to 4, the display device 100 may be set to the rotation state (S150). According to an example, when the pressure $F_{y2}$ sensed by the sensor 40 is greater than/equal to the first pressure $F_1$, the controller 20 may apply a control signal for turning on the first switch 510. The first current supplier 610 may supply current to the attenuator 400, more specifically, the first attenuating member 411 by the first switch 510 that has received an on signal from the controller 20.

For example, when current is supplied to the first attenuating member 411, the magnetism of the first attenuating member 411 may disappear, and accordingly, the first attenuating member 411 may be separated from the second attenuating member 412. As the first attenuating member 411 positioned on the display device 100 is separated from the second attenuating member 412 positioned on the main body 11, the display device 100 may change to the rotation state in which the display device 100 is freely rotatable with respect to the main body 11.

Also, the controller 20 may apply a control signal for turning on the second switch 520. The second current supplier 620 may supply current to the locking device 300, more specifically, to the first locking member 310 by the second switch 520 that has received an on signal from the controller 20.

When current is supplied to the first locking member 310, the magnetism of the first locking member 310 may disappear, and accordingly, the first locking member 310 may be separated from the second locking member 320. As the first locking member 310 positioned on the display device 100 is separated from the second locking member 320 positioned on the main body 11, the display device 100 may change to the rotation state in which the display device is freely rotatable with respect to the main body 11.

Then, the display device 100 may rotate with respect to the main body 11 (S160). For example, as the first attenuating member 411 positioned on the display device 100 is separated from the second attenuating member 421 positioned on the main body 11 and the first locking member 310 positioned on the display device 100 is separated from the second locking member 320 positioned on the main body 11, a constraint force of the display device 100 with respect to the main body 11 may be released. Accordingly, a user may rotate the display device 100 with respect to the main body 11 with a small force, thereby securing user convenience.

Figure 9:
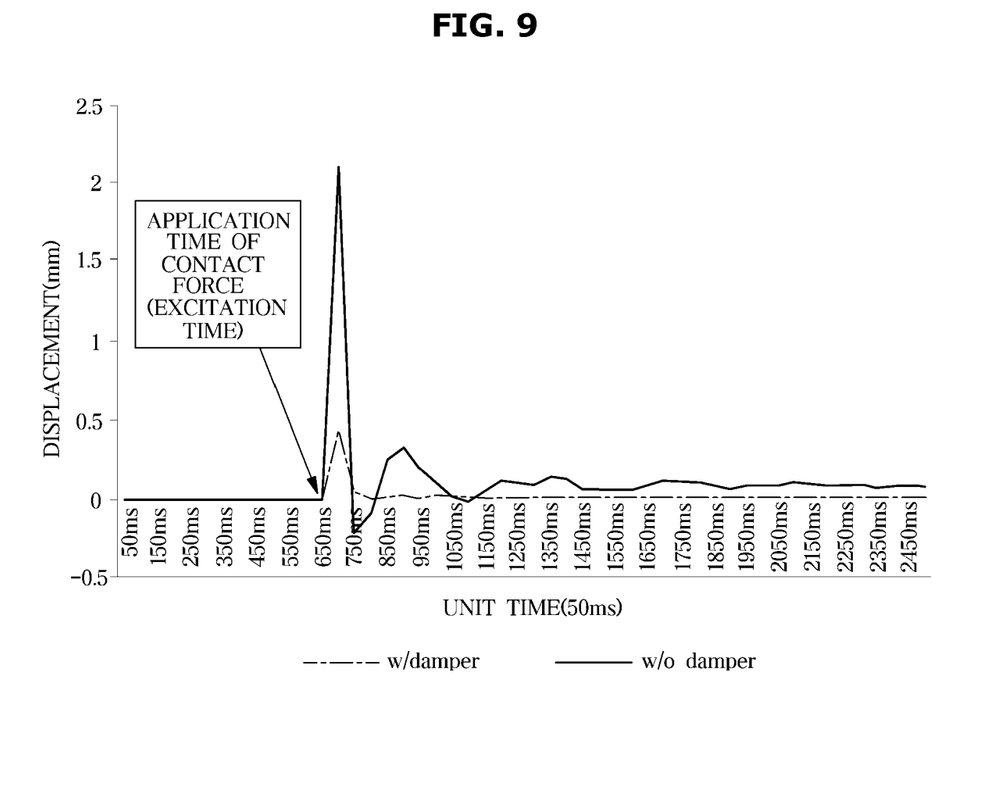
FIG. 9 is a graph obtained by measuring displacement of a display device per unit time according to existence and nonexistence of an attenuator in a medical apparatus according to an embodiment.

FIG. 9 is a graph obtained by measuring displacement of a display device per unit time according to existence and nonexistence of an attenuator in a medical apparatus according to an embodiment.

As shown in FIG. 7B, according to an embodiment, a user may apply pressure $F_3$ for inputting a touch input to the display device 100. In an embodiment, the locking device 300 and the attenuator 400 may be provided, whereas, in a comparative example, only the locking device 300 may be provided.

At this time, pressure applied to the display device 100 may be third pressure $F_{y3}$ that is perpendicular to one surface of the display 110 of the display device 100, a location at which the pressure is applied may be an upper end portion of the display device 100, and the pressure may be applied one time. In this case, a force corresponding to the third pressure $F_{y3}$ may include a magnitude of 300 gf to 400 gf, which is used for a general touch input. Through an experiment (measurement), movement displacement of the upper end portion of the display device 100 was measured under a condition that unit time is 50 ms (0.05 s) and total measure time is 2550 ms.

Referring to FIG. 9, in the comparative example in which the attenuator 400 is not positioned, a maximum displacement value of the upper end portion of the display device 100 was 2.09 m. This is a displacement level in which a human can recognize wobble with the naked eye. In the embodiment in which the attenuator 400 is positioned, a maximum displacement value of the upper end portion of the display device 100 was 0.45 mm. This is a displacement level in which a human cannot recognize wobble with the naked eye. A simple comparison between the measured values shows that there is a displacement difference of about 4.7 times according to existence and nonexistence of the attenuator 400.

In addition to the above-described embodiments, many other embodiments exist in the claims of the present disclosure. While numerous modifications and embodiments are allowed by the present disclosure, specific embodiments thereof are exemplarily illustrated in the drawings and described in detail in the detailed description. However, the embodiments are not intended for limiting the present disclosure to the disclosed specific forms but rather the present disclosure includes all modifications, equivalents, and alternatives matching with the spirit and technical range of the present disclosure.

The invention claimed is:

1. A medical apparatus comprising:
a main body including an inputter configured to receive a user command;
a display device positioned to be rotatable on one axis with respect to the main body, and extending along one plane;
a locking device configured to limit a rotation of the display device with respect to the main body when pressure being smaller than preset first pressure is applied to the display device along a direction that is perpendicular to one surface of the display device; and
an attenuator configured to attenuate a vibration of the display device with respect to the main body when pressure being smaller than the first pressure is applied to the display device along the direction that is perpendicular to the one surface of the display device,
wherein the locking device further comprises a first locking member positioned on the display device, and a second locking member positioned on the main body attached/detached to/from the first locking member,
when pressure being smaller than the preset first pressure is applied to the display device, the first locking member is attached to the second locking member and a rotation of the display device with respect to the main body is limited, and
when pressure being greater than or equal to the preset first pressure is applied to the display device, the first locking member is separated from the second locking member and the display device rotates with respect to the main body.

2. The medical apparatus of claim 1, further comprising a sensor configured to sense pressure applied to the display device along the direction that is perpendicular to the one surface of the display device.

3. The medical apparatus of claim 2, further comprising a controller configured to control operations of the attenuator and the locking device according to a magnitude of the pressure sensed by the sensor.

4. The medical apparatus of claim 1, wherein a plurality of attenuators are provided, and
the plurality of attenuators are spaced from each other with a preset distance from the locking device.

5. The medical apparatus of claim 1, wherein the attenuator comprises a first attenuator and a second attenuator, and
the first attenuator and the second attenuator are spaced from each other on an upper area of the display device.

6. The medical apparatus of claim 1, wherein the attenuator comprises a third attenuator and a fourth attenuator, and
the third attenuator and the fourth attenuator are spaced from each other on a lower area of the display device.

7. The medical apparatus of claim 1, wherein the attenuator further comprises:
a first attenuating member positioned on the display device; and
a second attenuating member positioned on the main body, and attached/detached to/from the first attenuating member.

8. The medical apparatus of claim 7, wherein the first attenuating member is attached to the second attenuating member by a magnetic force.

9. The medical apparatus of claim 8, wherein any one of the first attenuating member and the second attenuating member comprises a permanent magnet,
the medical apparatus further comprising:
a first current supplier configured to supply current to the permanent magnet; and
a first switch configured to turn on/off a connection between the first current supplier and the permanent magnet according to a magnitude of pressure applied to the display device.

10. The medical apparatus of claim 1, wherein the first locking member is attached to the second locking member by a magnetic force.

11. The medical apparatus of claim 10, wherein any one of the first locking member and the second locking member comprises a permanent magnet,
the medical apparatus further comprising:
a second current supplier configured to supply current to the permanent magnet; and
a second switch configured to turn on/off a connection between the second current supplier and the permanent magnet according to a magnitude of pressure applied to the display device.

12. A method for operating a medical apparatus including a main body and a display device hinge-coupled with the main body, the method comprising:
sensing pressure applied to the display device;
setting, when pressure being smaller than preset first pressure is applied to the display device, a mode of the display device to a use state in which a first locking member is attached to a second locking member and a rotation of the display device with respect to the main body is limited;
setting when pressure being greater than or equal to the preset first pressure is applied to the display device, a mode of the display device to a use state in which the first locking member is separated from the second locking member and the display device rotates with respect to the main body; and
attenuating, when the mode of the display device is set to the use state, a vibration of the display device with respect to the main body.

13. The method of claim 12, wherein the attenuating of the vibration of the display device comprises attaching a first attenuating member positioned on the display device to a second attenuating member positioned on the main body by a magnetic force,
wherein any one of the first attenuating member and the second attenuating member comprises a permanent magnet, and the remaining one comprises a magnet or a magnetic material capable of generating an attraction force with the permanent magnet.

* * * * *